United States Patent [19]

Barszcz et al.

[11] 4,415,664

[45] Nov. 15, 1983

[54] EPIAMINE-BASED SUPPORT MATRIX

[75] Inventors: Chester F. Barszcz, Chicago; Ted Symon, Lombard, both of Ill.

[73] Assignee: UOP Inc., Des Plaines, Ill.

[21] Appl. No.: 411,158

[22] Filed: Aug. 25, 1982

[51] Int. Cl.$^3$ .................... C12N 11/14; C12N 11/08; B01J 31/02; B32B 17/10

[52] U.S. Cl. .................... 435/176; 428/441; 428/451; 435/180; 502/172

[58] Field of Search ............ 428/411, 417, 448, 441, 428/451, 457, 458, 426, 324, 525; 252/430, 428; 435/174, 176, 180, 181

[56] References Cited

U.S. PATENT DOCUMENTS

| | | | |
|---|---|---|---|
| 4,141,857 | 2/1979 | Levy et al. | 252/430 |
| 4,193,910 | 3/1980 | Rohrbach et al. | 260/42 |
| 4,206,259 | 6/1980 | Rohrbach et al. | 428/304 |
| 4,218,363 | 8/1980 | Rohrbach et al. | 260/42.14 |
| 4,250,080 | 2/1981 | Rohrbach et al. | 260/42.46 |
| 4,292,199 | 9/1981 | Rohrbach et al. | 252/428 |
| 4,337,172 | 6/1982 | Teague et al. | 252/428 |
| 4,343,901 | 9/1982 | DeFilippi | 252/430 |

*Primary Examiner*—George F. Lesmes
*Assistant Examiner*—Beverly Johnson
*Attorney, Agent, or Firm*—James R. Hoatson, Jr.; Eugene I. Snyder; William H. Page, II

[57] ABSTRACT

A support matrix is described where a porous inorganic support is impregnated with an amine-bearing polymer whose backbone is polar and hydrophilic. The amino groups are cross-linked and themselves bear pendant aldehyde groups kept well away from the surface of the polymer-coated support.

12 Claims, No Drawings

EPIAMINE-BASED SUPPORT MATRIX

BACKGROUND OF THE INVENTION

Because enzymes can catalyze chemical transformations so effectively, there is increasing emphasis on the use of enzyme reactions in commercial processes. The relatively high cost of enzymes demands their reuse. Typically, if the reaction is performed under homgeneous conditions recovery of enzyme is difficult and expensive, which effectively precludes homogeneous enzymatic catalysis. The solution to this problem is to insolubilize enzyme under conditions where a substantial portion of the enzymatic activity exhibited in solution remains under heterogenous reaction conditions.

One particular solution to the aforementioned problem is the construction of immobilized enzyme systems. An immobilized enzyme system consists of a support matrix to which there is bound an enzyme. A support matrix is a structure characterized as having good physical integrity and favorable properties toward liquid flow under conditions experienced in fixed bed reactors, and further characterized by having the ability to bind or immobilize enzymes with minimum perturbation of enzymatic action. By an immobilized enzyme system is meant the structure which results from immobilization of an enzyme on a support matrix.

The binding or immobilization of enzymes to a support matrix is represented by the extremes of physical and chemical binding forces. It is to be recognized that in most cases enzyme immobilization arises from a combination of such binding forces, although often one such force predominates, with the nature of enzyme immobilization generally being determined by the nature of the support matrix. As an example, when the support matrix is a resin, such as one of the phenol-formaldehyde type, binding is predominantly through physical forces. A similar result is obtained when the support matrix is of an ion exchange type. Where the support matrix is comprised of refractory inorganic material, such as inorganic oxides, glass, and ceramics, bearing or impregnated with organic material, for example, polyamines, either bearing pendant functional groups themselves or cross-linked with a bifunctional reagent which provides pendant functional groups, enzyme immobilization arises mainly by chemical reaction of a site on the enzyme with the pendant functional group so as to form a covalent bond. In such an instance binding is, at least predominantly, by chemical means.

The support matrix of U.S. Pat. No. 4,141,857, which enjoys wide commercial utility, is an inorganic porous support impregnated with a polyamine cross-linked with an excess of a bifunctional reagent so as to afford pendant functional groups. In such a support matrix the amino groups are in the backbone of the polyamine, that is, where polymeric amines are used the amino groups are part of the polymer chain.

In contrast, the patentees of U.S. Pat. Nos. 4,193,910, 4,206,259, 4,218,363, and 4,250,080 describe a support matrix where the amino groups of the polyamine are pendant to a polyethylene polymer backbone which is completely nonpolar and highly hydrophobic.

In some applications it is desirable to have a support matrix where the amino groups are pendant to a polymer backbone which is hydrophilic, but which otherwise retains the features and advantages of the previously described support matrices. The support matrix of this invention provides the attributes of a polar, hydrophilic polymer bearing pendant amino groups, which is a combination unknown in the prior art.

The invention described herein relates to support matrices, and immobilized enzyme system therefrom, comprising an inorganic porous support impregnated with a polymer having a hydrophilic backbone and bearing pendant polyamines which are cross-linked with dialdehydes, and whose amino groups bear pendant aldehyde groups. One advantage of the instant invention arises because the polar and hydrophilic polymer presents a different, generally more natural environment to a subsequently bound enzyme than is the case where the polymer is nonpolar and hydrophobic. Another advantage of the invention described accrues from the pendancy of the polyamines which themselves bear pendant aldehyde groups ultimately engaged in covalent bonding to enzymes, resulting in the enzyme being further away from the surface of the support matrix than is the case in prior art materials and thereby presenting an environment more closely analogous to that of soluble enzymes than was previously possible.

DESCRIPTION OF THE INVENTION

The invention described herein is a support matrix comprising a porous, inorganic support impregnated with an epiamine cross-linked with an excess of a dialdehyde so as to furnish pendant aldehyde groups.

The porous inorganic supports which may be utilized in the practice of this invention include refractory inorganic oxides such as alumina, silica, thoria, magnesia and combinations thereof. Other materials which can be used include ceramics and porous glass. Alumina is a preferred support and gamma-alumina is a particularly preferred support.

The porous inorganic support is impregnated with an epiamine. An epiamine is the reaction product of an epihalohydrin homopolymer, or a copolymer of epihalohydrin and epoxyalkane monomers, of molecular weight between about 1,000 and 100,000 with an amine. Among the suitable amines are alkylenediamines containing from 2 to about 10 carbon atoms, although alkylene groups containing 2 or 3 carbon atoms are preferred. Linear alkylene groups are more commonly employed than are branched alkylene groups, but the latter may be used, although not necessarily with equivalent results in all cases. Examples of linear alkylene groups include ethylene, propylene, butylene, amylene, hexylene, heptylene, octylene, nonylene, and decylene. Examples of branched alkylene groups include isopropylene, sec-butylene, isobutylene, sec-amylene, isoamylene, and so forth. Ethylenediamine, 1,2- and 1,3-diaminopropane are diamines of choice. Amines such as a lower molecular weight poly(ethyleneamine) also may be successfully used in this branch of the invention, and include materials such as diethylenetriamine, triethylenetetramine, tetraethylenepentamine and pentaethylenehexamine.

The epiamines of this invention are the reaction product of about 1 molar proportion of amine or polyamine per one equivalent poly(epichlorohydrin), an equivalent of poly(epichlorohydrin) being defined as an amount containing 1 gram atomic weight of chlorine.

Impregnation of the porous inorganic support with epiamine usually occurs by contacting the support with an aqueous solution of the epiamine. In one variant the epiamine is cross-linked prior to impregnation in order to increase its molecular weight. The cross-linking agents which may be used have the general formula X(CH$_2$)$_n$X, where n is an integer from 2 to about 8, and X may be a halogen, isocyanate group or COY group, where Y is a halogen. Thus, the cross-linking agents include alpha, omega dihalides, diisocyanates and acid halides from dicarboxylic acids.

Illustrative examples of cross-linking agents include 1,2-dichloroethane, 1,3-dibromopropane, 1,4-diiodobutane, succinoyl chloride, glutaroyl bromide, adipoyl fluoride, pimeloyl chloride, suberoyl fluoride, azaleoyl bromide, sebacoyl chloride, 1,5-dicarbonylaminopentane, 1,6-dicarbonylaminohexane, 1,7-dicarbonylaminoheptane, and 1,8-dicarbonylaminooctane.

Another class of cross-linking agents which may be utilized have the formula,

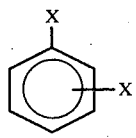

where X may be defined as in the prior paragraph.

Generally the porous support and solution of epiamine are contacted with mixing for a time sufficient to ensure impregnation, which is between about 0.5 to about 3 hours. Excess polyamine is then removed as by decantation or filtration, and the polyamine-impregnated porous support is then advantageously dried prior to further treatment, although drying is not absolutely necessary.

Next, the epiamine impregnated support is treated with an excess of a dialdehyde sufficient to furnish pendant aldehyde groups as well as to cross-link the epiamine. The dialdehydes used in this invention have the formula OHC(CH$_2$)$_p$CHO, where p is an integer from about 2 to about 10. Aromatic dialdehydes, especially phthalaldehydes, also may be advantageously used with glutaraldehyde being a preferred aldehyde. Illustrative examples of suitable aldehydes include succinaldehyde, glutaraldehyde, adipaldehyde, pimelaldehyde, suberaldehyde, azelealdehyde, and sebacaldehyde.

An excess of dialdehyde is used, which means that at least 3 moles of dialdehyde per mole of amino group of epiamine is furnished. The dialdehyde will be furnished in an aqueous solution where possible, although alcoholic solutions also may be used, although not necessarily with equivalent results. Contacting generally occurs with intermittent mixing for a time between about 0.5 and about 5 hours, after which unreacted aldehyde is removed as by decantation. The support matrix is then washed well with copious quantities of water until the washings give a negative Fuchsin aldehyde test. The resulting support matrix is then dried, usually in air, and is in a state for binding of enzymes.

Immobilized enzyme systems may be prepared from the support matrix described above merely by contacting a solution of the enzyme with a support matrix at an appropriate pH. It is to be recognized that the pH used will depend upon the tolerance of the enzyme to various conditions of acidity or alkalinity, and is not necessarily related to the ease of reaction of an enzyme amino group with an aldehyde group from the support matrix. Contacting generally occurs at or below room temperature, although with some stable enzymes immobilization at temperatures up to about 70° C. may be performed. Among the enzymes which may be immobilized in this way, which list is to be considered as illustrative rather than exhaustive, are included glucose isomerase, glucoamylase, cholesteroloxidase, alcohol dehydrogenase, amino acid oxidase, arginase, asparaginase, catalase, chymotrypsin, cellulase, collagenase, deoxyribonuclease, ficin, histidase, lactase, peroxidase, lysozyme, the amylases, papain, rennin, ribonuclease and urease.

The example given below merely illustrates this invention and is not intended to limit it in any way.

EXAMPLE

A polyamine-impregnated gamma alumina was prepared by mixing 6 ml of a 2 percent aqueous solution of epiamine per gram of support for 1 hour. The epiamine was prepared by heating ethylenediamine to 100°–110° C. and adding to it slowly with stirring an epichlorohydrin homopolymer, of about 2500 average molecular weight, at a ratio of 1 mole equivalent chloromethyl group per 6 moles of ethylenediamine. Heating and stirring were continued for 3 hours. The reaction mixture was then cooled and the HCl formed was neutralized with a 20% aqueous NaOH solution. The precipitated NaCl was removed by filtration and the excess ethylenediamine was removed by vacuum distillation. The resulting viscous product was diluted with water just prior to impregnation of the catalyst support.

Excess aqueous solution was removed by filtration and the solid was air dried. The epiamine-impregnated alumina was then contacted with intermittent mixing with a 1 percent aqueous solution of glutaraldehyde (10 ml/g support) with degassing for about 1 hour. Excess solution was removed by decantation, and the resulting solid was throughly washed with water until a negative Fuchsin aldehyde test was obtained. This completed the preparation of the support matrix, which can be dried and stored until use is desired.

A solution of glucose isomerase containing 398 units of enzyme per ml of solution was contacted with the support matrix prepared above, in an amount of 12 ml solution per gram support matrix, at 4° C. for about 16 hours. Residual enzyme solution was removed by decantation and the immobilized enzyme system was washed well with deionized water, then loaded into a reactor.

A feedstock of 45 percent by weight Cerelose (a purified glucose) containing 1,000 ppm Na$_2$SO$_3$, 5 millimoles per liter MgSO$_4$, and 7 ppm sodium omadine at a pH 8.0–8.1 was used at 60° C. and the reactor was operated at a liquid hourly space velocity to ensure 42±1 percent conversion to fructose. An immobilized glucose isomerase system so prepared had an initial activity of 710 units per gram with a half-life of about 59 days.

What is claimed is:

1. A support matrix comprising a porous inorganic support selected from the group consisting of alumina, silica, thoria, magnesia, porous glass, ceramics, and combinations thereof, impregnated with an epiamine cross-linked with an excess of a dialdehyde selected from the group of dialdehydes with the formula OHC(CH$_2$)$_p$CHO, where p is an integer from 2 to about 10, and "phthalaldehyde, wherein the epiamine is the reaction product of poly(epichlorohydrin) with an alkylenediamine containing from 2 to about 10 carbon atoms."

2. The support matrix of claim 1 where the support is alumina.

3. The support matrix of claim 1 wherein the alkylenediamine is ethylenediamine, 1,2-diaminopropane, or 1,3-diaminopropane.

4. The support matrix of claim 1 where the epiamine is the reaction product of poly(epichlorohydrin) with a polyamine selected from the group consisting of diethylenetriamine, triethylenetetramine, tetraethylenepentamine, and pentaethylenehexamine.

5. The support matrix of claim 1 where the dialdehyde is glutaraldehyde.

6. A method of making a support matrix comprising impregnating a porous inorganic support selected from the group consisting of alumina, silica, thoria, magnesia, porous glass, ceramics and combinations thereof with an epiamine, "wherein the epiamine is the reaction product of poly(epichlorohydrin) with an alkylenediamine containing from 2 to about 10 carbon atoms," removing excess epiamine, contacting the impregnated support with an excess of a dialdehyde selected from the group consisting of dialdehydes with a formula $OHC(CH_2)_pCHO$, where p is an integer from 2 to about 10, and phthalaldehydes, removing unreacted dialdehyde, and recovering the resulting support matrix.

7. The method of claim 6 where the support is alumina.

8. The method of claim 5 where the alkylenediamine is ethylenediamine, 1,2-diaminopropane, or 1,3-diaminopropane.

9. The method of claim 6 where the epiamine is the reaction product of poly(epichlorohydrin) with a polyamine selected from the group consisting of diethylenetriamine, triethylenetetramine, tetraethylenepentamine, and pentaethylenehexamine.

10. The method of claim 6 where the dialdehyde is glutaraldehyde.

11. An immobilized enzyme system comprising the support matrix of claim 1 having an enzyme covalently bonded thereto.

12. The immobilized enzyme system of claim 11 where the enzyme selected from the group consisting of glucose isomerase, glucoamylase, cholesteroloxidase, alcohol dehydrogenase, amino acid oxidase, arginase, asparaginase, catalase, chymotrypsin, cellulase, collagenase, deoxyribonuclease, ficin, histidase, lactase, peroxidase, lysozyme, the amylases, papain, rennin, ribonuclease and urease.

* * * * *